(12) United States Patent
Bacus et al.

(10) Patent No.: US 6,226,392 B1
(45) Date of Patent: *May 1, 2001

(54) METHOD AND APPARATUS FOR ACQUIRING AND RECONSTRUCTING MAGNIFIED SPECIMEN IMAGES FROM A COMPUTER-CONTROLLED MICROSCOPE

(75) Inventors: James V. Bacus, Downers Grove; James W. Bacus, Oakbrook, both of IL (US)

(73) Assignee: Bacus Research Laboratories, Inc., Elmhurst, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/395,694

(22) Filed: Sep. 13, 1999

Related U.S. Application Data

(63) Continuation of application No. 08/805,856, filed on Mar. 3, 1997, which is a continuation-in-part of application No. 08/701,974, filed on Aug. 23, 1996.

(51) Int. Cl.⁷ ..................................... G06F 15/00
(52) U.S. Cl. .......................... 382/128; 382/133; 382/128; 382/224; 382/240; 382/284; 382/294; 348/79; 356/39; 356/372; 600/407; 250/455; 345/435; 364/413.07; 364/413.13; 128/922
(58) Field of Search .................................... 382/240, 224, 382/128, 284, 294, 133; 348/79; 356/372, 39; 600/407; 250/455; 345/435; 128/922; 364/413.07, 413.13

(56) References Cited

U.S. PATENT DOCUMENTS

| | | | |
|---|---|---|---|
| 4,742,558 | 5/1988 | Ishibashi et al. | 382/240 |
| 4,760,385 * | 7/1988 | Jansson | 340/709 |
| 5,216,596 | 6/1993 | Weinstein | 348/79 |
| 5,252,487 | 10/1993 | Bacus et al. | 436/63 |
| 5,257,182 | 10/1993 | Luck et al. | 382/224 |
| 5,297,034 | 3/1994 | Weinstein | 382/128 |
| 5,428,690 | 6/1995 | Bacus et al. | 382/128 |
| 5,499,097 | 3/1996 | Ortyn et al. | 356/372 |
| 5,836,877 * | 11/1998 | Zavislan | 600/407 |

* cited by examiner

Primary Examiner—Andrew W. Johns
Assistant Examiner—Hieu C. Le
(74) Attorney, Agent, or Firm—Fitch, Even, Tabin & Flannery

(57) ABSTRACT

A method is disclosed for using a computer controlled microscope system to provide a reconstructed, seamless image from several contiguous fields of view to show the architecture and spatial relationship of biological material in a specimen. The specimen is scanned with a microscope and a digital scanner to provide digitized titles of contiguous, fields of view at a predetermined magnification, optical resolution and pixel resolution. Preferably, an automated X, Y stage with higher positional spatial resolution than the spatial pixel resolution of the digital scanner is used to acquire the contiguous fields of view and the image registration information which is used to reconstruct and to display on a monitor the reconstructed image formed of the contiguous multiple fields of view. Preferably, a macro image of contiguous image tiles at a low magnification and optical resolution is obtained and the user navigates within the macro image and selects areas. Higher magnification titles for the selected area are assembled and viewed at a higher magnification and optical resolution as a composite micro image of the selected area. Both the macro and micro images may be displayed simultaneously. Preferably, the user may scroll and cause additional fields of view to be added to previously displayed fields of view.

11 Claims, 16 Drawing Sheets

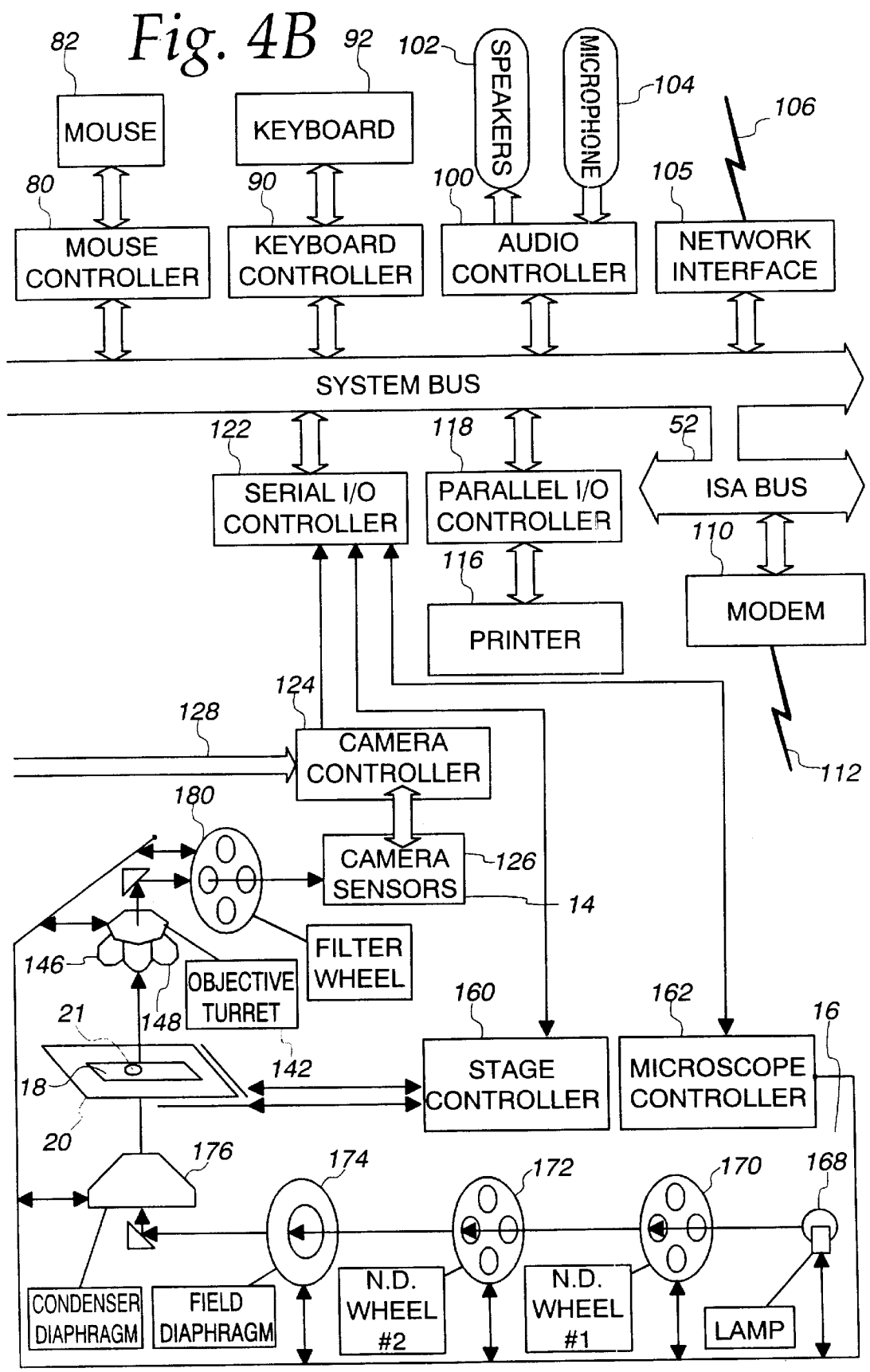

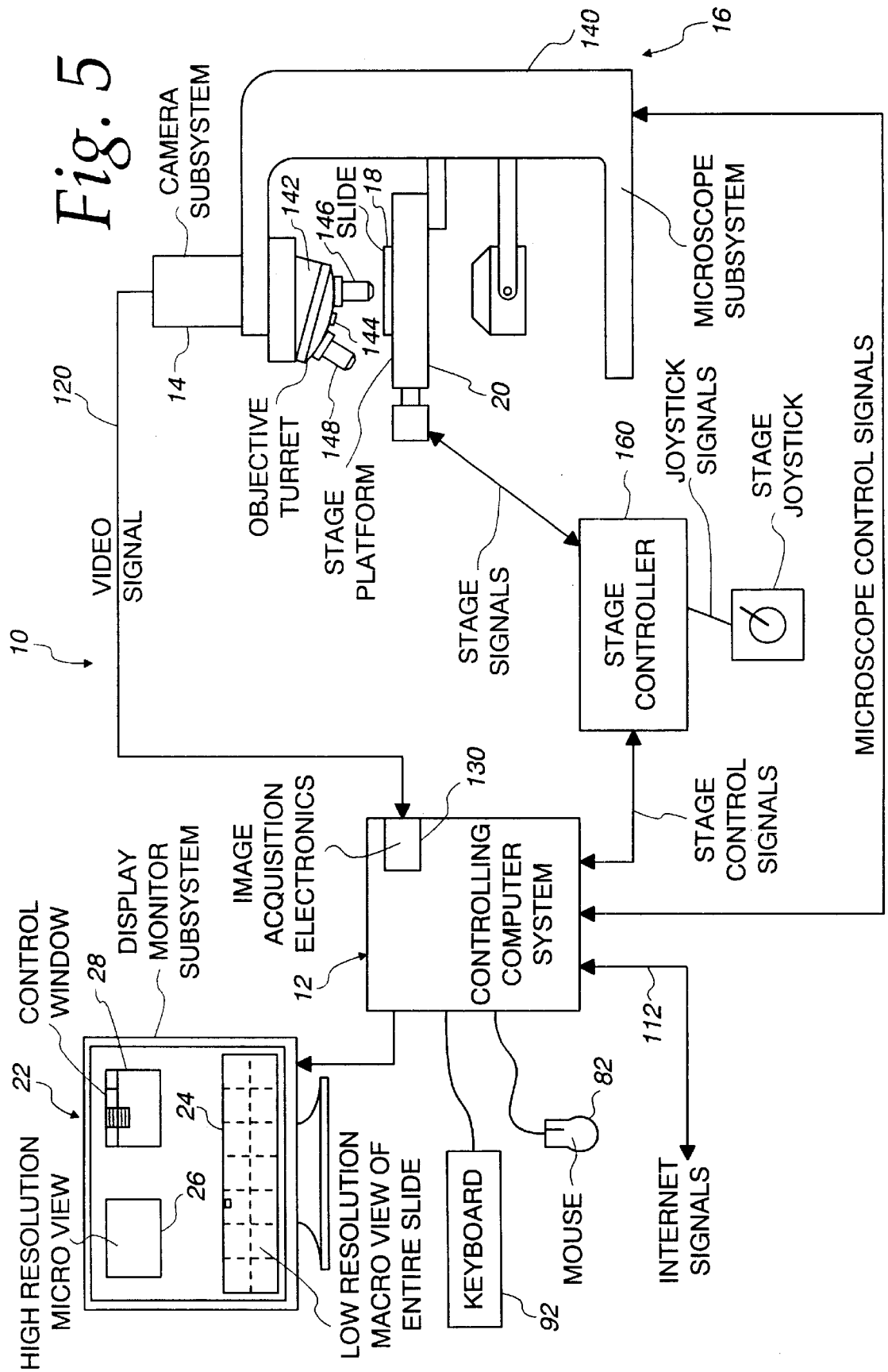

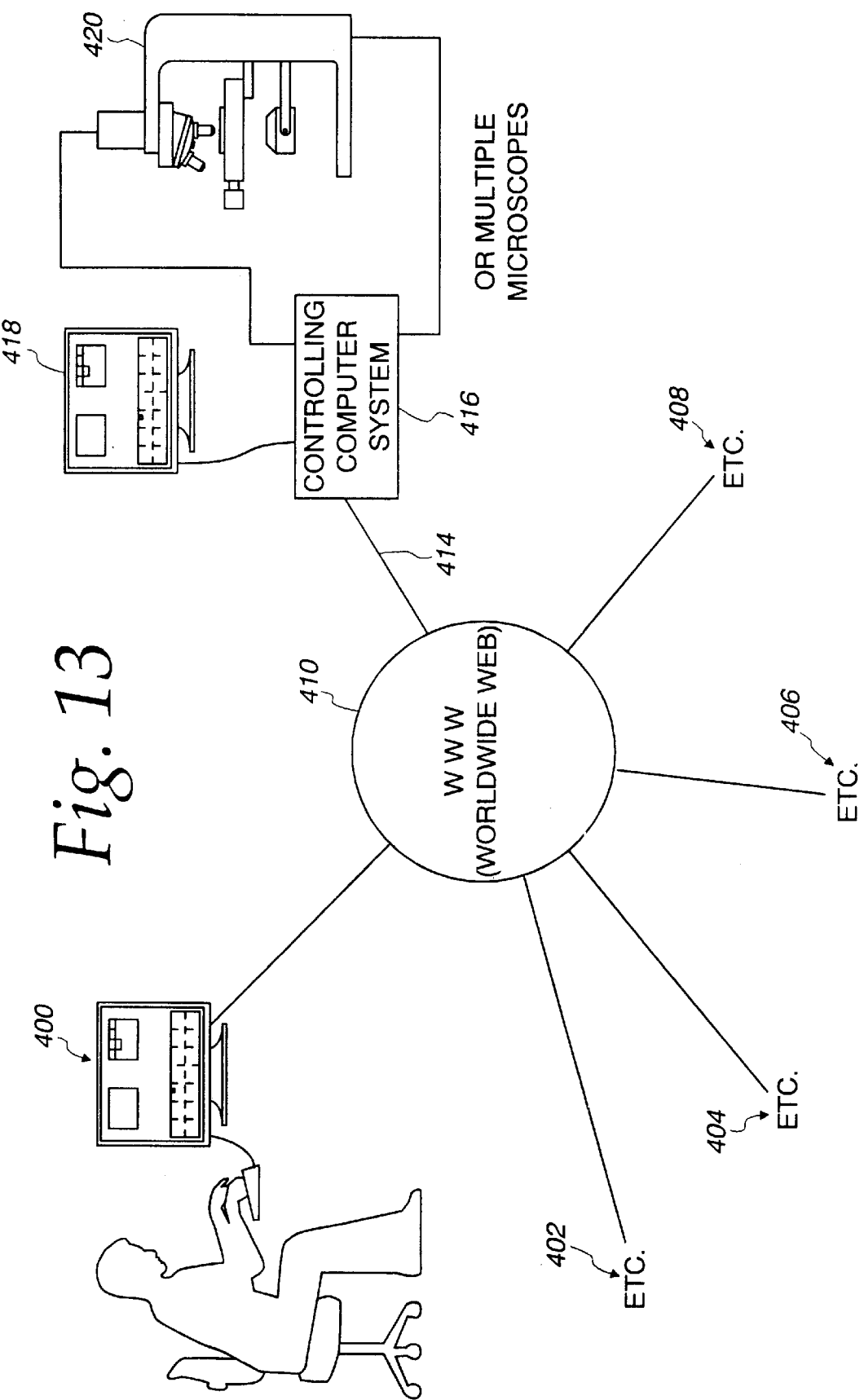

METHOD AND APPARATUS FOR ACQUIRING AND RECONSTRUCTING MAGNIFIED SPECIMEN IMAGES FROM A COMPUTER-CONTROLLED MICROSCOPE

CROSS REFERENCE TO RELATED APPLICATIONS

This is a continuation of co-pending U.S. application Ser. No. 08/805,856, filed Mar. 3, 1997, which is a continuation-in-part of co-pending U.S. application Ser. No. 08/701,974, filed Aug. 23, 1996.

FIELD OF THE INVENTION

This invention relates to a method of and apparatus for acquiring and analyzing digital images of an image viewed through a computer-controlled automated microscope and more particularly, to using the latter in a quantitative analysis of plant of biological specimens.

BACKGROUND OF THE INVENTION

In the image analysis and quantification of DNA from tissue sections as disclosed in U.S. Pat. No. 4,741,031, and also especially in the immunohistochemistry assays on the kinds of cell analysis systems disclosed in U.S. Pat. Nos. 5,086,476; 5,202,931; and 5,252,487 issued to Bacus, there is a problem of first locating the cancer regions for analysis under low power and then remembering them when performing the analysis under higher power. Specifically, the problem is that once the microscope is set up for quantitation by image analysis under, e.g. 40×, where all of the diaphragms are set and light adjusted, etc., if the operator needs to move to another tissue area, it is first desirable to locate it at e.g. 10×. In fact, often regions can only be located at this power. In order to do so however, all of the settings (diaphragms, light levels, wavelengths of light, etc.) have to be changed to view the tissue at this magnification. Currently, there is no way to ensure that one could go back to the settings at the previous 40× magnification and continue on with the quantitative image analysis of that same specimen. This necessitates finding those areas under 40×, without changing objectives, which is very slow and time-consuming, and often important cancer areas can be missed.

Also, another problem with tissue analysis, at its current state-of-the-art, is that it is not completely automated, for example, with regard to finding structural regions such as glands, basal layers or other important diagnostic regions. However, as set forth in my co-pending patent application Ser. No. 701,974, filed Aug. 23, 1996, if these regions are located, important very sensitive diagnostic measurements can be performed, which patent application is incorporated by reference as if fully reproduced herein. For example, as disclosed in the aforesaid patent application, assays are made of a variety of tissue types, both human and animal for analysis of neoplasia in tissue, for pre-invasive cancer in tissue, and the effects on the tissue of chemopreventive agents. A quantitative analysis by image processing techniques is performed on tissue types, having various architectural features, such as breast tissue, colon tissue, prostate tissue, esophageal tissue, skin tissue, cervix tissue, etc. These tissues have different morphologies, and they undergo different neoplasias usually resulting from a cellular mutation, as may be enhanced by a carcinogen, or resulting from a cellular proliferation rate enhanced by hormones, growth factors, or other inducers of abnormal tissue growth. Often it is desired to quantify small changes in the neoplasia when it is incipient or through a series of analyses performed at close time intervals to measure whether the neoplasia progression is increasing or has been slowed, stopped or regressed.

Usually, the tissue specimens are cut to expose the basal layer for review under the microscope. Typically, the quantitative measurements are performed at 40× to obtain 100 to 400 tissue images. The 40× objective provides a narrow field of view of a very small portion of the entire basal layer. Often, the basal layer is somewhat elongated and generally linear such as a basal layer in a rat esophagus; and the analysis of the basal layer requires examining it along its length. The basal layer in a mouse colon is more in the form of an irregular, circular shape; and the analysis of this basal layer requires traveling about this circular shape. In breast tissue samples, suspected tumor areas may be at widely-spaced points in the stained tissue; and one wants to be able to navigate and travel to these specific suspected areas and to do the 40× analysis at these areas in an efficient manner. There is a need to allow an experienced operator to interact with the analysis to locate and identify such regions in an interactive manner. Especially, an interactive manner that would be familiar and consistent with the use of a microscope manually, with higher power magnification and low power magnification simultaneously available, but performed on a computer terminal. Such a level of interaction is different than the interaction with the system disclosed in the above-listed Bacus Patents. There is a need to take the level of interaction to a higher level and let each component, the human and the computer, perform the part that it does best, in the most cost-effective manner.

There are available on the marker computer-controlled, automated microscopes such as those sold by Carl Zeiss, Inc., Thornwood, N.J., under the name Axioplan 2 for taking photographic images of a specimen in the microscopic field of view. Those particular microscopes have computer-controlled and automatically adjusted subsystems, such as an illumination subsystem, a focusing subsystem, a diaphragm or optical stops subsystem, an objective lens subsystem, or a filtering subsystem. As an operator selects changes from one objective lens, such as one providing low magnification, e.g., 4×, to a higher magnification, e.g., 40×, the computer-automated system will turn the lens turret to switch in the high magnification automatically and adjusts the lens and also automatically adjusts the illumination to eliminate glare and to provide the proper light illumination including light density. Further, the focus is adjusted, and the proper diaphragm openings are automatically rest. Thus, the computer-controlled, automated subsystems automatically rest to values stored and predetermined for each selected objective lens and the analysis being done.

Those particular microscopes can be used to view various objects or specimens, but are most typically used to view and to take still photographs of biological specimens, such as tissues and cells. Those particular microscopes lack a computer-controlled X and Y stage for translating a specimen-carrying slide with respect to the field of view of the selected objective lens. Currently, pathologists and others who use such microscopes want to view the specimen images in full color or in enhanced colors using fluorescent illumination and/or monochromatic images using the automated filter subsystems on the microscopes. Currently trained pathologists or clinicians are accustomed to manually adjust and have a microscope available to them to view larger areas of the specimen at low magnification, and then to momentarily switch in a new higher magnification lens to obtain a more highly magnified image of a portion of the specimen viewed at low magnification. Pathologists and those working in this area have created in themselves a desire to view suspect tissue through a microscope and appear to resist analysis systems that do not provide them this ability.

The microscopic filed of view reduces very substantially as the magnification increases. The skill level of the clinician and/or pathologist is important to locate viewing the most suspicious areas or points of interest on the specimen. Sometimes, a technician will do a first assay and analysis. A pathologist will return to the selected points of interest or other points of interest for review and analysis. One concern with respect to a quantitative analysis of breast cancer tissue or prostate biopsy tissue samples to pap smears or other tests for various cancers or the like is that a particularly suspicious point in the tissue may be overlooked and missed during the visual assay or for selection for an automated review analysis. When observing at high magnifications, the field of view is limited to very small area of the specimen. Hence, the observer has difficulty in knowing and remembering the actual, exact location of this small periscopic view within the very large whole specimen.

Often, also the problem is finding or locating the tissue or cells for view at high magnification so that artifacts and/or blank spaces on the slide are not viewed. A number of approaches have been proposed to prescreen and locate by an X and Y address the cells or small points of interest from a very large number of potential points of interest.

There are currently available commercial services for prescreening pap smears where one can mail in slides and the service will do a microscopic prescan at high magnification for suspected or suspicious areas of interest which are marked and given address locations, and also a video tape of the slide specimen is returned by this service to the sender. The sender then reviews the areas of interest located during the prescreening and/or the video tape to complete the analysis.

In an attempt to locate and allow review of specified points of interest, U.S. Pat. No. 5,428,690 to Bacus discloses a system for prescreening of a field of cells on a specimen slide at low magnification before the viewer. When seeing a point of interest to be viewed at high magnification, the viewer will operate a switch or the like to select and record the address of these selected prescreened points of interest. Later, these prescreened points of interest are then brought into position to be analyzed at high magnification. This system is too slow for many uses.

A very expensive system is currently in use in which a pathologist located at a diagnostic center is able to make a diagnostic opinion with respect to specimens under a microscope at a remote center. The pathologist at the diagnostic center manipulates robotic controls to send telepathology signals via a special, dedicated satellite or other large bandwidth channel to control the microscope at the remote site in approximately real time. The pathologist then can maneuver the remote microscope to shift the microscope's field of view and to send, by telepathology, a highly magnified, very small image back to the pathologist. This system requires each subscriber to have a special microscope operable by manipulation of the robotic controls at the diagnostic center and a dedicated or large bandwidth channel to convey real time video signals and hence results in a very high cost for the assay being done. To assist the pathologist in staying within the specimen at the remote site, a peripheral edge or map of the specimen is made using a second video camera and a light box or by using computerized scanning equipment to trace the outline or peripheral edge of the specimen boundaries. A small circle of light is displayed within the map of the specimen so that the pathologist at the diagnostic center knows the location of the field of view of the highly magnified image within the specimen. In a sense, the pathologist is operating in real time in the same way that he would use his own microscope at his diagnostic center except for a slight transmission delay used to transmit the video signals of the highly magnified image over large bandwidth channel. Although the pathologist has a small map or peripheral outline of the specimen, the pathologist's field of view of the actual specimen is only the small circle of view that is coming through the microscope objective lens. This does not help the pathologist locate suspicious areas of interest as in a prescreening of the entire tissue. The pathologist may switch to the lowest magnification to get the largest field of view of a small section of the specimen, but he never views the entire specimen at any magnification. Also, there is no image analysis quantitative testing from the received images at the diagnostic center; and no quantitative assaying is done with these images at the diagnostic center.

There is a particular interest today in using the Internet system because it is so readily accessible by users at a low cost and using a computer and viewing screen connected to the computer. One problem with trying to do any transmission of digitized, microscopic, highly magnified images over the Internet is that the bandwidth is too narrow to accommodate the tremendous amount of stored data which needs to be transmitted. There is a need for a system which would allow a pathologist or another person, to be able to perform tissue analysis or quantitative assays using a standard computer terminal from a location remote from the automated microscope.

SUMMARY OF THE INVENTION

In accordance with the present invention, a person such as a pathologist at a computer terminal may control an automated microscope to acquire on a computer screen or window images of the specimen at different magnifications as selected by the person. Further, the person may receive on the screen a low magnification, reconstructed image of the entire specimen to aid the person in interactively selecting points of interest on the specimen, such as along a basal layer of a tissue specimen.

More specifically, and in accordance with the present invention, the microscope's small field of view limitation of a specimen is overcome by providing to the viewer a reconstructed, digitized and magnified image of the entire specimen (or a very large portion of the specimen) for performing a visual analysis of the entire tissue in full color to aid in the selection of points of interest to be viewed at a higher magnification. This is achieved by acquiring a large number of low magnification images of the specimen through a microscopic scanning system, e.g., 35 image tiles of the specimen at 1.25×, and then assembling and coordinating the tiles to form an overall, low magnified image of the specimen, i.e., a macro image of the specimen. Preferably, the digitized macro image is reduced in size by a software system to a smaller size, e.g., a ¼ size image that is displayed on a local screen or is sent over a low band width or a high bandwidth channel to a remote screen. Thus, the pathologist not only does not need to have others do a slow laborious prescreening to locate suspicious areas for analysis or for viewing at high magnification, he can use his own experiences to go directly to the most suspicious areas which he sees on the macro image. He can, on a priority basis, do the most suspicious area first, followed by lower priority areas of interest.

In accordance with the present invention, there is provided a new and improved automated, computer-controlled microscope that displays the low magnification composite image of the specimen to allow the user to view and to interactively select points of interest, each of which may be displayed at high magnification. This is achieved by providing the user with a marker, such as a cursor or the like, to select the defined area of interest; and to acquire reproduced, spatially adjacent high magnification, digitized images of the selected area of interest. More specifically, the specimen, when it was first scanned at low magnification to provide a macro view of the specimen, the addresses or locations of the tile images and/or pixels for the composite image were acquired. Therefore, any selected region of interest in the macro image has locations to which the microscopic stage may be automatically repositioned under a changed, higher magnification lens to acquire higher magnification, digitized image tiles that can be assembled into a micro image. Herein, both the macro and micro images are formed of adjacent digitized image tiles which have been coordinated to reproduce spatially the original image that was scanned.

It is the high magnification images, usually at 40×, that were analyzed using image processing techniques as disclosed in the aforesaid patent application, to provide an assay or numerical histological data for the specimen.

In accordance with the preferred embodiment of the invention, the pathologist may select a larger region for analysis at high resolution than can be accommodated at this magnification on his high magnification viewing screen. He can, though, view all of the adjacent, highly magnified, digitized image tiles on this high magnification screen by scrolling up or down or right to left to shift these digitized, adjacent image tiles into view on the screen. Thus, even at a higher magnification of a region the pathologist is able to obtain a much larger view than the small field for the objective lens in use of adjacent tissue or cells to give him a broader, overall perspective of what is happening or what has happened in a specific section of a specimen. For instance, a pathologist may want to see at high magnification and to assay at this high magnification, a suspicious area, the pathologist can draw a mark about the area and cause it to then be assayed and displayed.

By having displayed on a low magnification screen or split screen of the full composite area, by having the high magnification region being marked on the low image screen, and by having the region being scrolled to view adjacent high magnification images on the high magnification screen, the pathologist has available information to guide him in the sense of helping to navigate intelligently within the specimen in his search for cancerous tissue or the like for further inspection of measurement of malignant characteristics. Often, when restricted to a field of view of an objective microscope, the pathologist has a difficult time, in the words of a cliche, of seeing the forest for the trees. In the present invention, the pathologist has a full, magnified, reduced in size specimen view with the higher image area marked thereon to guide him and to let him see the forests. He can also see a region of the forest at higher magnification by scrolling adjacent trees images onto the high magnification screen.

In accordance with a further aspect of the invention, the user may elect to change to an intermediate magnification being viewed by either switching automatically to a new objective lens and acquiring new digitized image tiles at the intermediate magnification or by using software to reconstruct from the existing high and low magnification, digitized images a new intermediate magnification digitized image.

The preferred, low magnification image, which is reduced in size, can be transmitted over narrow bandwidth channels such as a local area network or over the Internet through various servers and computers. Likewise, the reconstructed, high magnification images can be transmitted over such narrow band width channels. Because the microscope is fully computer controlled, a pathologist or other person having a split screen computer such as a PC, can be connected to the microscope and operate it from a remote location to obtain the macro image and to navigate to points of interest and obtain the desired micro images. With the present invention, there is no need for a specialized microscope at each remote location nor for a broadband channel to send video signals in real time between the diagnostic center and the remote location.

BRIEF DESCRIPTION OF THE DRAWINGS

FIG. 5 is a block diagram of a portion of the apparatus shown in FIG. 4 showing details of a mechanical arrangement of a microscope;

FIG. 13 is a block diagram of a remote networked system for distributing and accessing diagnostic images and data through a hypertext transport protocol based server directly or over a packet network;

DETAILED DESCRIPTION OF THE PREFERRED EMBODIMENT

Figure 1:
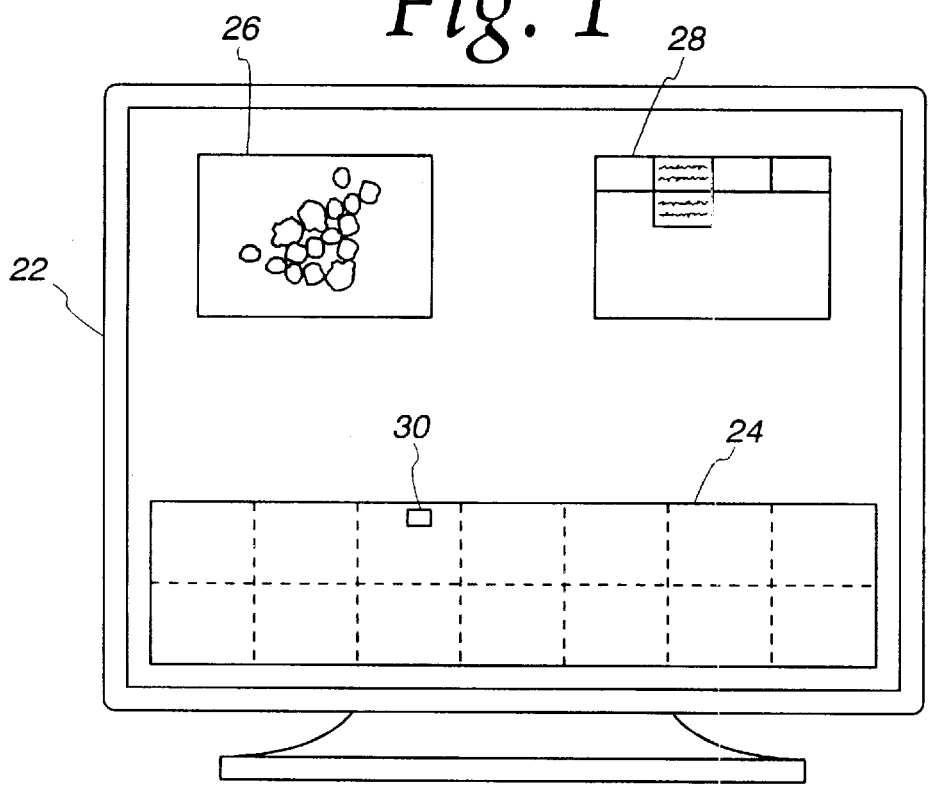
FIG. 1 is a screen view of a system embodying the present invention showing a low magnification image of a specimen on a microscope slide in one window, a high magnification image of a portion of the low magnification image selected by a region marker and a control window.
Figure 3:
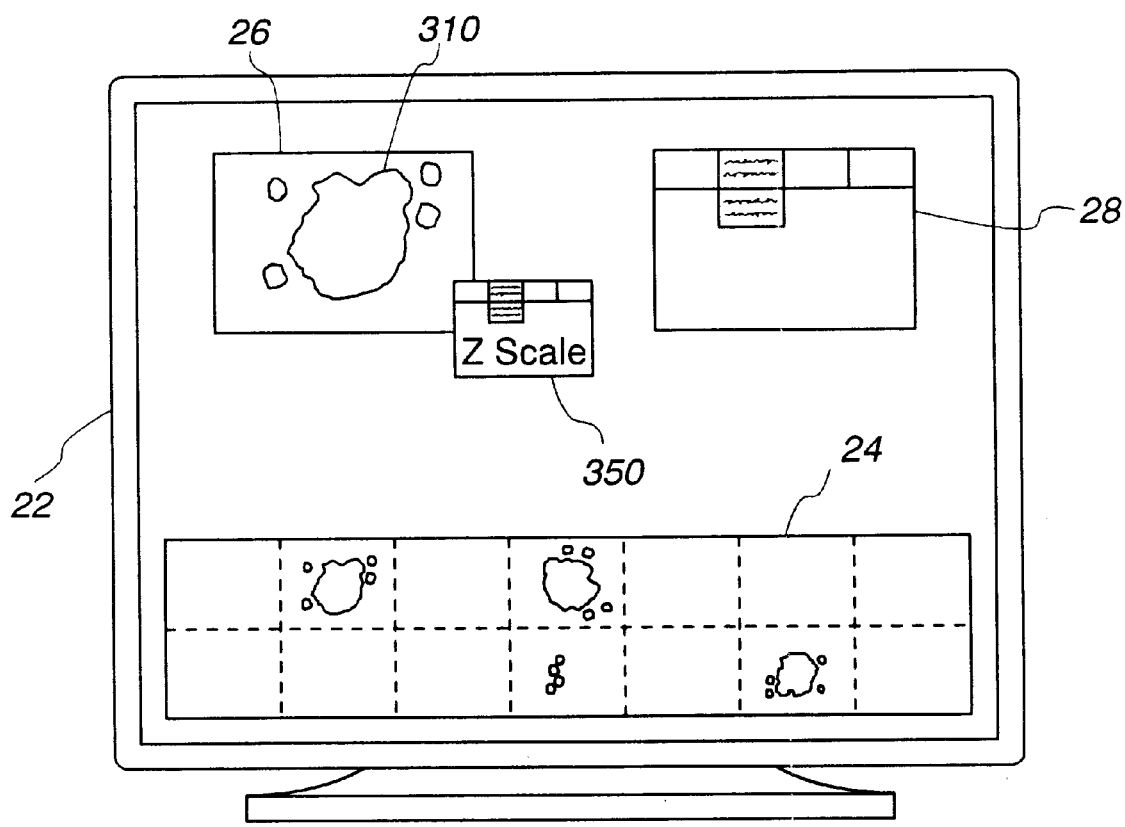
FIG. 3 is a view similar to FIG. 2 including the control window but also including a low magnification region from the slide showing regions marked by a histology grade or structure through automatic analysis of tissue and a high magnification window showing markings related to the grading or histology grade yielded by the automatic analysis of tissue in combination with a window showing a numerical score.
Figure 4A:
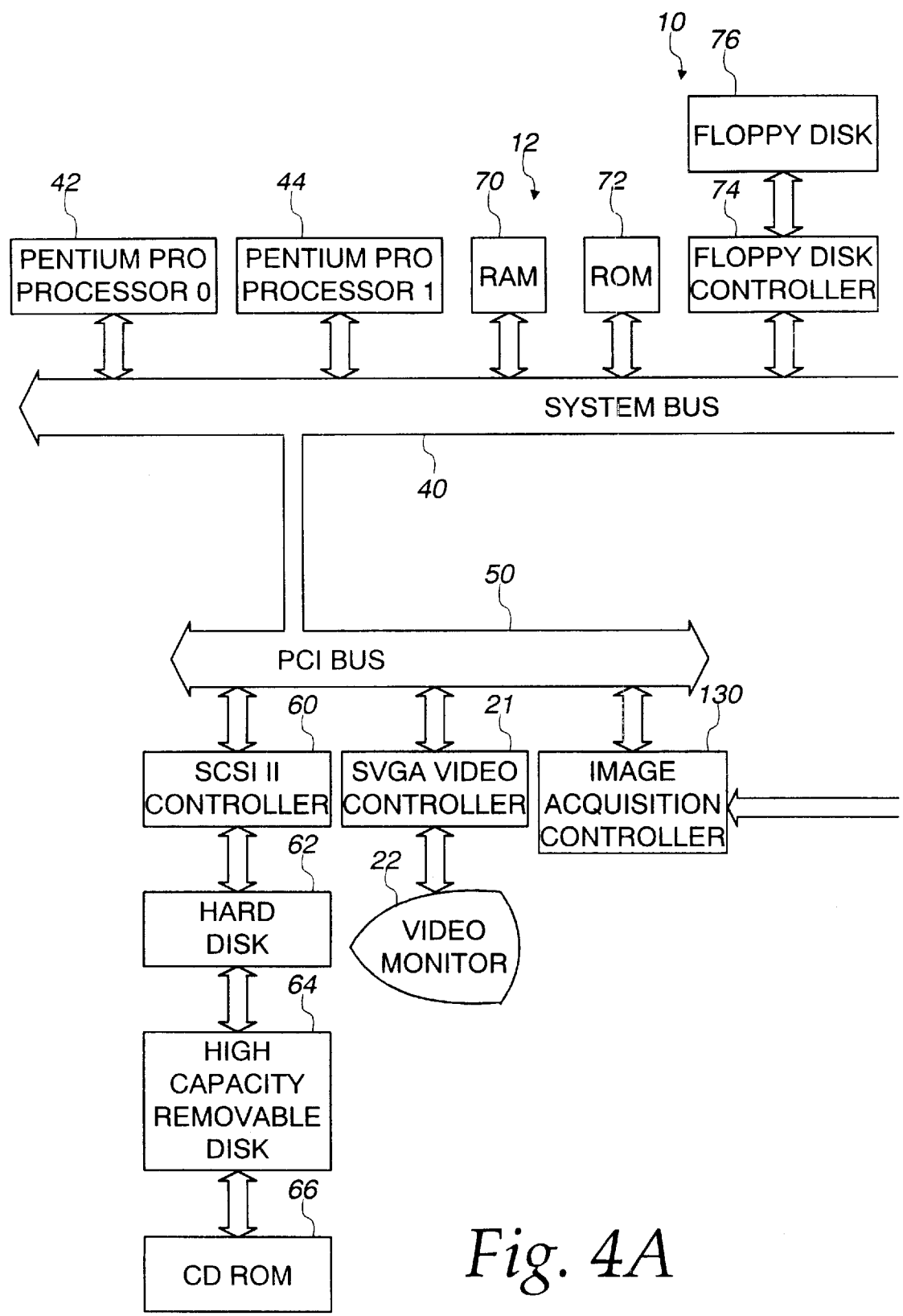
FIG. 4 is a block diagram of the apparatus embodying the present invention.

Referring now to the drawings, and especially to FIGS. 4 and 5, apparatus for synthesizing low magnification and high magnification microscopic images is shown therein and generally identified by reference numeral 10. The system includes a computer 12 which is a dual Pentium Pro personal computer in combination with a Hitachi HV-C20 video camera 14 associated with a Zeiss Axioplan 2 microscope 16. The computer system 12 is able to receive signals from the camera 14 which captures light from the microscope 16 having a microscope slide 18 positioned on an LUDL encoded motorized stage 20. The encoded motorized stage 20 includes a MAC 2000 stage controller for controlling the stage in response to the computer 12. A microscope slide 18 includes a biological specimen 21 which is to be viewed by the microscope and whose image is to be digitized both at low magnification and at high magnification as selected by a user. The low magnification digitized image is then displayed on a 21 inch Iiyama video display monitor 22 having resolution of 1600 by 1200 to provide display screens of the type shown in FIGS. 1 through 3 including a low magnification image 24, for instance, at 1.25 power, a high magnification image 26, for instance at 40 power and a control window or image 28. The low magnification image may have identified therein a region 30 which is reproduced at high magnification in high magnification screen or window 26 so that a pathologist or other operator of the system can review architectural regions of interest in low magnification image 24 and simultaneously view them in high magnification in the high magnification screen or window 26 to determine whether the cells forming a portion of the architectural feature need be examined further for cancer or the like or not.

The computer 10 is constructed around a PCI system bus 40 and has a first Pentium Pro microprocessor 42 and a second Pentium pro microprocessor 44 connected thereto. The system bus 40 has connected to it a PCI bus 50 and an ISA bus 52. The PCI bus 50 has a SCSI controller 60 connected thereto to send and receive information from a hard disk 62. The hard disk 62 also is coupled in daisy chain SCSI fashion to a high capacity removal disk and to a CD Rom drive 66. The hard disks 62 contains the programs for operating the system for controlling the microscope 16 and for processing the images as well as for doing a quantitative analysis of the selected portions of the histological specimens being viewed on the slide 18. The system bus 40 also has connected to it a random access memory 70 within which portions of the program being executed are stored as well as a read only memory 72 for holding a bootstrap loader as well as portions of the basic input/output operating system. A floppy disk controller 74 is coupled to the system bus 40 and has connected to it a floppy disk drive 76 for reading and writing information to a floppy disk as appropriate. A mouse controller 80 is coupled to the system bus and has a mouse 82 which operates as a pointing device for controlling manipulations on the screen 22 and within the windows 24, 26 and 28. A keyboard controller 90 is connected to the system bus and has a keyboard 92 connected thereto. The keyboard 92 may be used to send and receive alphanumeric signals to other portions of the computer. An audio controller 100 has a plurality of speakers 102 and a microphone 104 connected thereto for audio input and output and is coupled to the system bus 40. A network interface, such as a network interface card 104, is connected to the system bus and can provide a signals via a channel 106 to other portions of a network or internet to which the system may be connected. Likewise, signals can be sent out of the system through a modem 110 connected to the ISA bus 52 and may be sent via a channel 112, for instance, to the Internet. A printer 116 is connected via a parallel I/O controller 118 to the system bus in order to provide printouts as appropriate of screens and other information as it is generated. A serial I/O controller 122 is connected to the system bus and has connected to it a camera controller 124 which is coupled to CCD sensors 126 in the cameras. The CCD sensors 126 supply pixel or image signals representative of what is found on the slide 18 to an Epix pixci image acquisition controller 130 coupled to the PCI bus 50.

The microscope 16 includes a base 140 having a stage 20 positioned thereon as well as an objective turret 142 having a plurality of objectives 144, 146 and 148 thereon. The objective 144, for instance, may be of 1.25×objective. The objective 146 may be a 20×objective. The objective 148 may be a 40×objective. Signals from the camera sensors and controller are supplied over a bus 128 to the image acquisition system where they are digitized and supplied to the PCI bus for storage in RAM or for backing storage on the hard disk 62.

Figure 6:
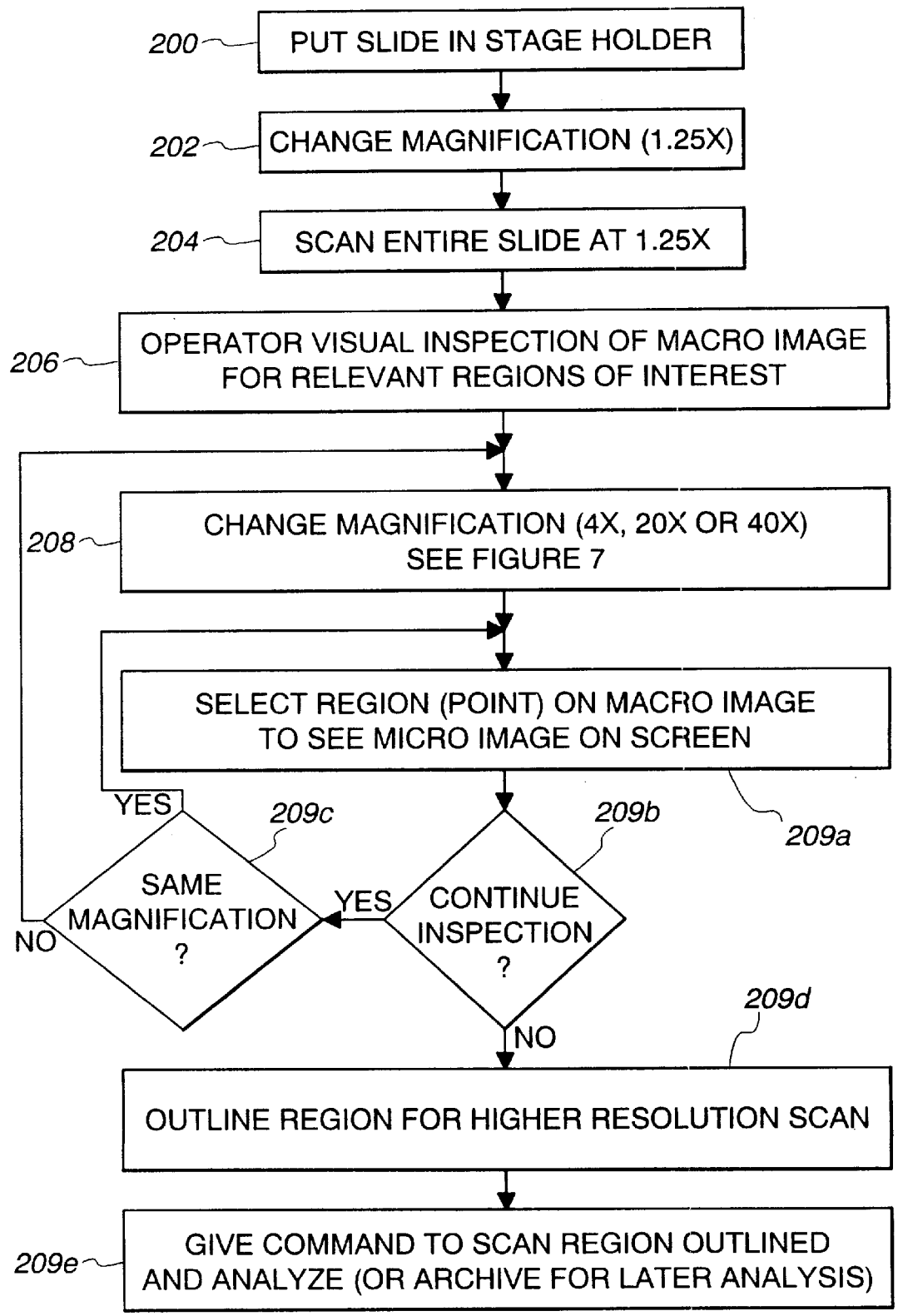
FIG. 6 is a flow diagram related to operation of the apparatus.

When a specimen is on the slide 18 the stage 20 may be manipulated under the control of the computer through a stage controller 160 coupled to the serial I/O controller 122. Likewise, a microscope controller 162 controls aspects of the microscope such as the illumination, the color temperature or spectral output of a lamp 168 and the like. For instance, in normal operation, when a specimen is placed on the slide, specimen slide 18 is placed on the stage 20 in a step 200, as shown in FIG. 6, the processors 42 and 44 send a command through the system bus to cause the serial I/O controller 122 to signal the microscope controller to change magnification to 1.25× in a step 202. This is done by rotating the objective turret of the Axioplan 2 microscope to select the objective 144. Likewise, the controller sets the color temperature of the lamp 168, sets a pair of neutral density filter wheels 170 and 172 and sets a field diaphragm 174 for the correct illumination. A condenser diaphragm 176 is also controlled and a color filter wheel 180 may also be controlled to apply the appropriate filter color to the CCD censors 126 in the camera. The entire slide is then scanned in a step 204. The images are tiled and melded together into the overall image 24 supplied on the screen 22 to provide the operator in the step 206 with a visually inspectable macro image of relevant regions of the slide of interest.

In order to provide the magnified image, the mouse may be moved to identify a marker segment or region which, for instance, may be a rectangular region (as shown as 30 in FIG. 1) which will cause the microscope to change magnification as at step 208 to 4×, 20×, 40×, etc., by rotating the turret to bring the appropriate objective lens system into viewing position.

Next the user, in a step 209a, uses the mouse to select the region on the macro image in order to select the micro image to be viewed on the screen 22. In a step 209b a test is made to determine whether the user has commanded continued inspection. If the user has, a test is made in a step 209c to determine if the magnification is to be changed by changing the selected objective. In the event the magnification is to be changed control is transferred to the step 208. If the magnification is to remain unchanged control is transferred to the step 209a. In the event inspection is not to continue the region selected is outlined for higher magnification scan in a step 209d. In a step 209e, a command may be received to scan or acquire the higher magnification image for display in screen 26. The image may then be archived for later analysis, displayed or analyzed immediately.

In order to perform the magnification called for in step 208, the overall illumination and control of the microscope will be controlled so that in a step 210 the objective turret 142 will be rotated to place the higher power objective above the slide 18. In a step 212 voltage to the lamp will be changed to adjust the lamp 168 to provide the proper illumination and color temperature as predetermined for the selected objective. In a step 214, the condenser diaphragm 176 will have its opening selected as appropriate to provide the proper illumination for that objective. In a step 216, the filter turret 180 will select the proper light wavelength filter to be supplied to the camera sensors. For instance, a red, blue or green filter, as appropriate, particularly if the specimen has been stained. In a step 218 the field diaphragm 174 will have its opening changed. In a step 220 the neutral density filter wheel 170 will select a neutral density filter and in a step 222 the neutral density filter wheel 172 will also select a neutral density filter. In a step 224 the X, Y and Z offsets will be used for reconstruction of the recorded image at the magnification and in a step 226 the current position will be read from encoders in the stage which are accurate to 0.10 micron.

Figure 9:
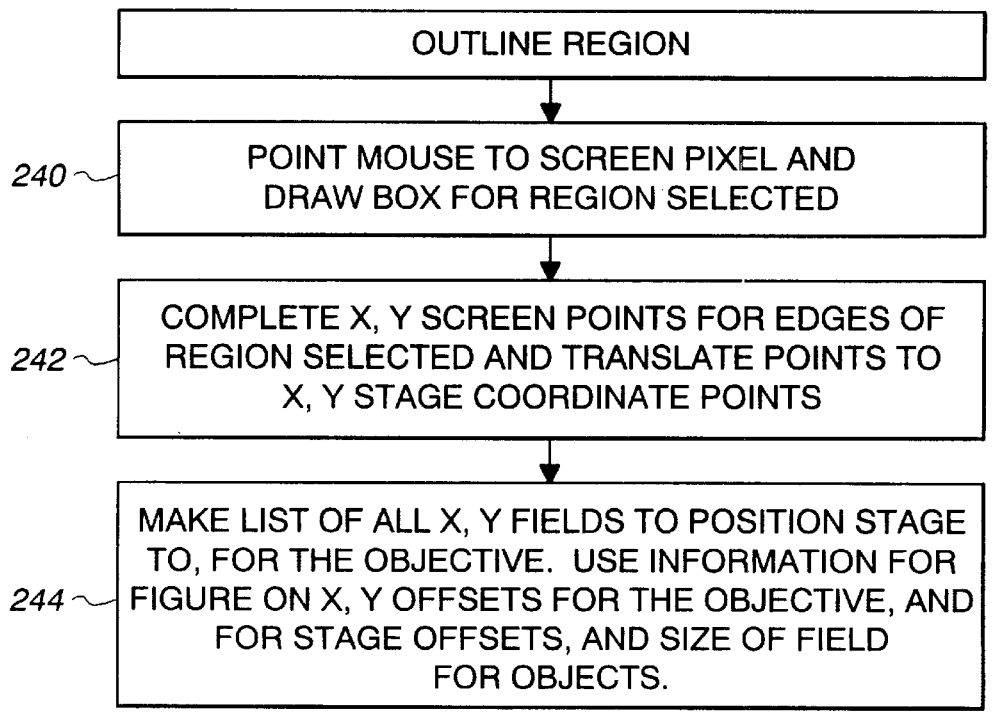
FIG. 9 is a flow chart for a region outlying routine.

In order to identify the selected region the mouse is moved to that area of the region in a pointing operation in a step 240 as shown in FIG. 9. The mouse may be moved to draw a box around the region selected. In a step 242 the X and Y screen points are computed for the edges of the regions selected and the computed image or pixel points are translated to stage coordinate points in order to control the stage of the microscope. In a step 244 a list of all of the X fields for positioning the stage for the objective is stored in random access memory and may be backed up on the hard disk. The information from the X offsets for the objective and the stage offsets is used as well as the size of the field to position the slide properly under the objective to capture the micro image.

Figure 10:
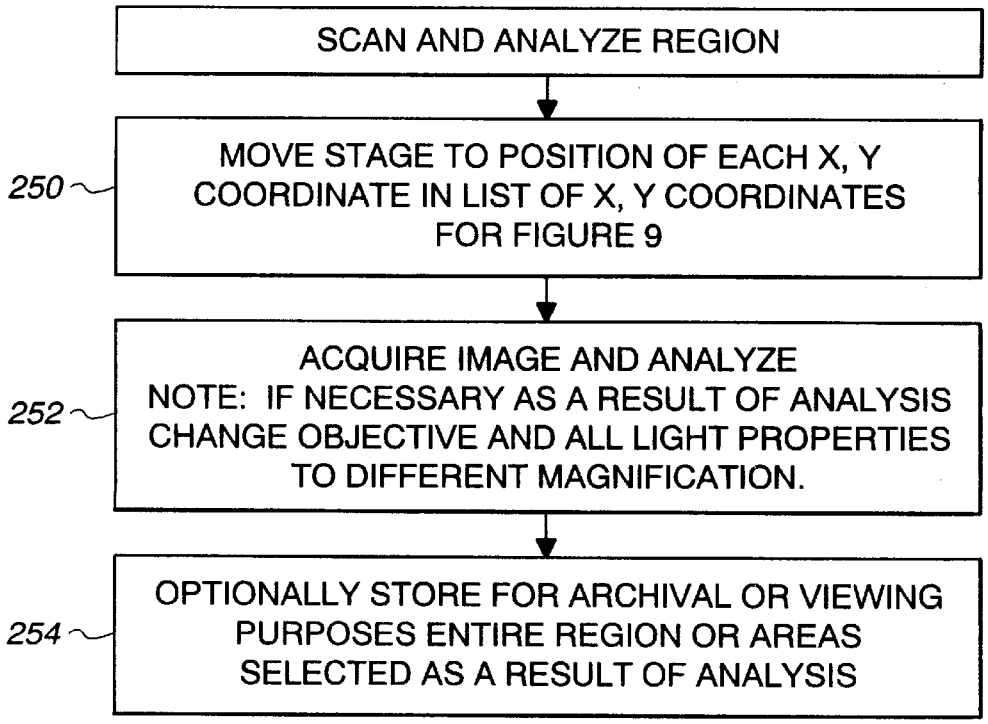
FIG. 10 is a flow chart for a scanning and analyzing routine.

When the slide has been positioned properly, as shown in FIG. 10 in a step 250 the stage is positioned for each of the X and Y coordinate values in stage coordinate values and the digitized image is captured by the cameras and stored in RAM and backed up on the hard disk. The image showing the architecture and spatial relationship of biological material in the biological specimen may be then analyzed quantitatively in various manners such as those set forth in the previously-identified United States application. Optionally the image may be stored for archival purposes in a step 254.

Figure 7:
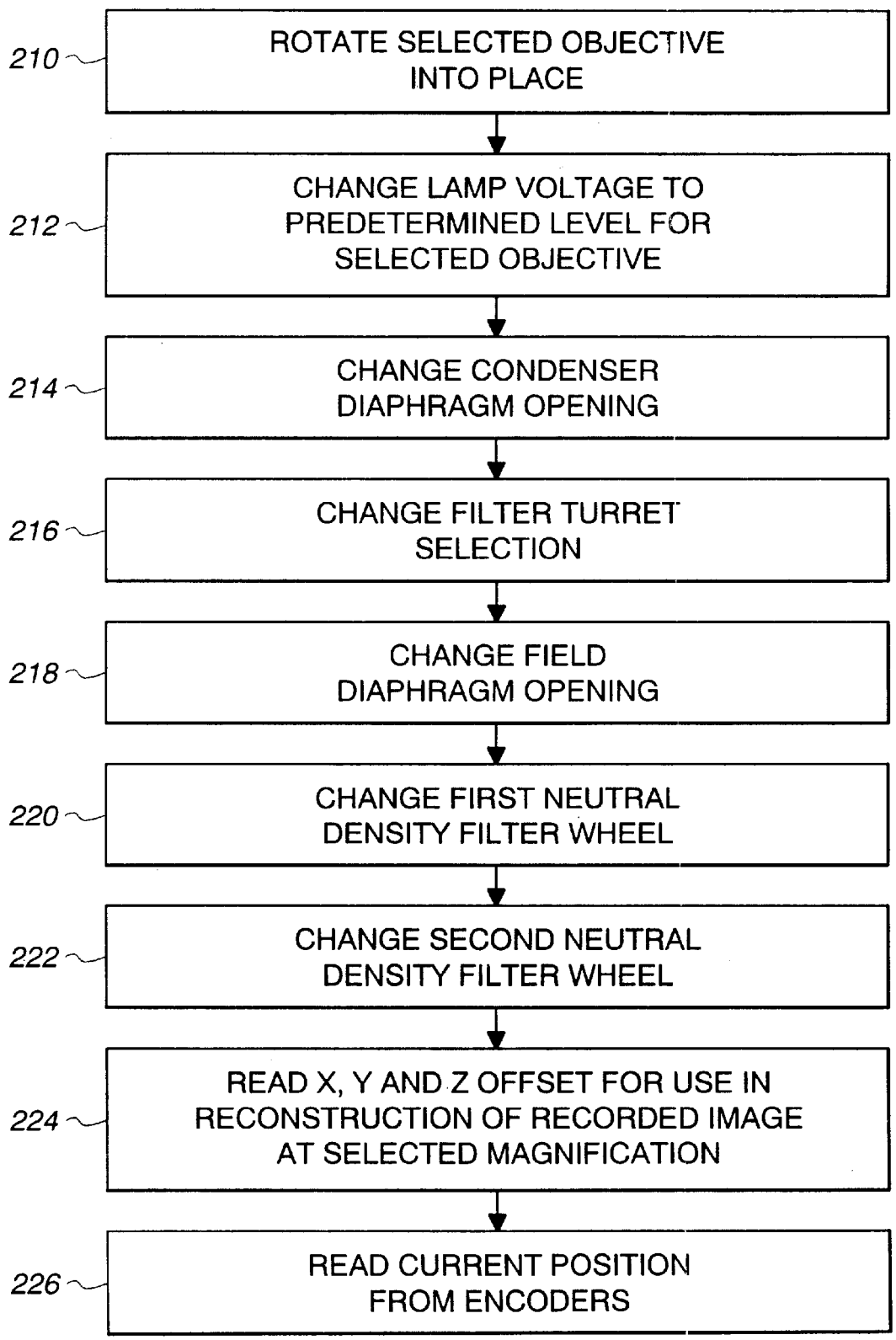
FIG. 7 is a flow diagram of details of one of the steps in FIG. 6.
Figure 8:
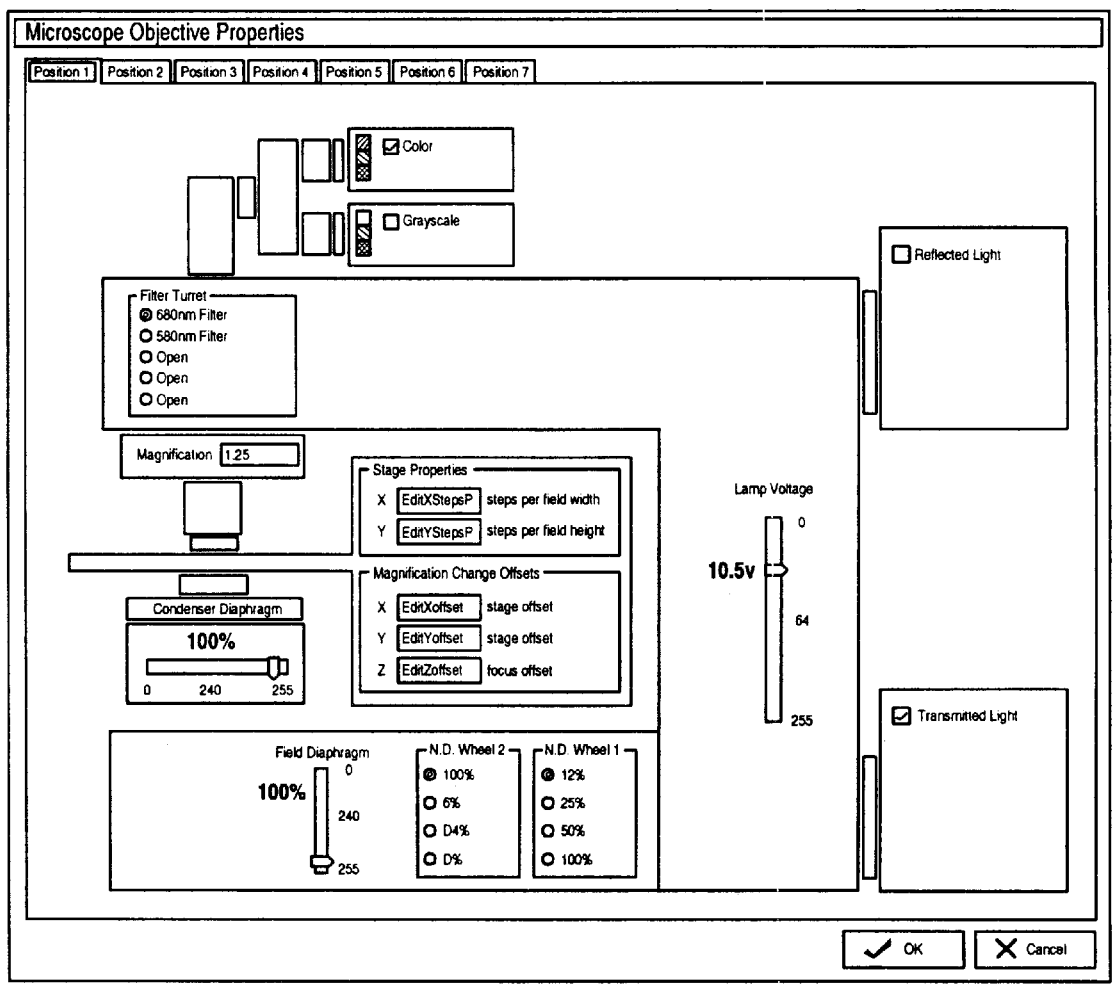
FIG. 8 is a display screen showing control parameters to be manipulated thereon.

In order to override the specific control functions that take place as shown in FIG. 7, a screen is provided as shown in FIG. 8 wherein the XY step size can be edited, the X, Y and Z offset can be edited, the lamp voltage can be selected, the neutral density filter can be selected as well as the opening of the field diaphragm and several other microscopic characteristics. FIG. 8 is a view of the settings of the microscope objective properties of the Axioplan 2, computer-controlled microscope.

Figure 2:
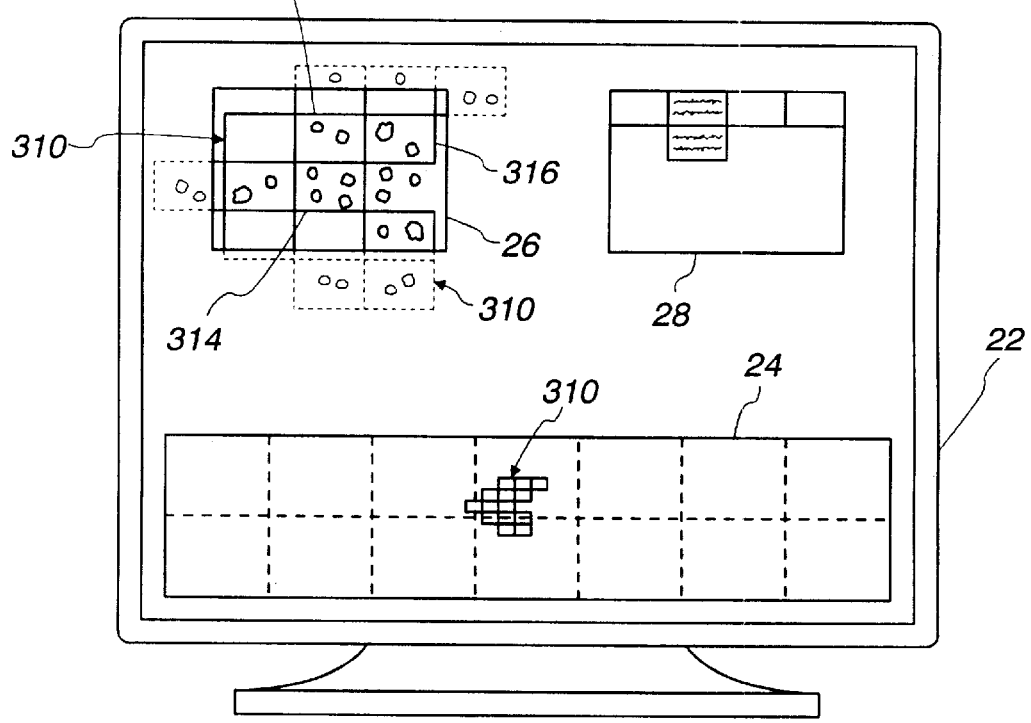
FIG. 2 is a view of a display screen of the apparatus embodying the present invention showing the control window a low magnification window having a plurality of high magnification micro image regions delineated therein and a high magnification window including one or more of the micro image regions.
Figure 11:
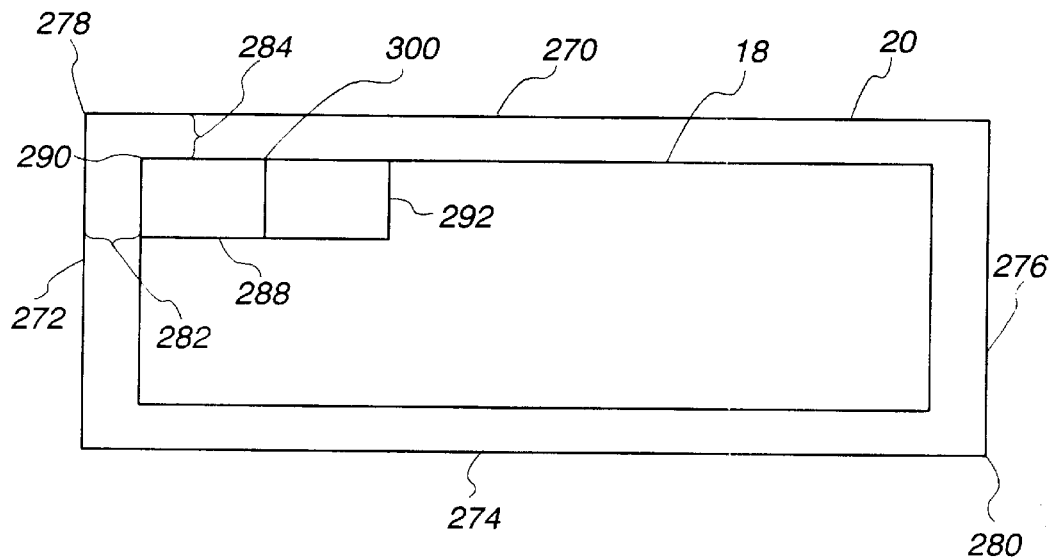
FIG. 11 is a schematic showing of the limits of travel of the microscope stage with respect to the image tiles.

The X and Y positioning is specifically carried out as shown in FIG. 11 where the slide 18 is shown with a slide boundaries 270, 272, 274 and 276. Stage boundary for limits of the stage travel for purposes of the stage the stage can be moved all the way from an upper left hand corner of travel 276 to a lower right hand corner of travel 280. At the upper left hand bounded corner of travel 278 limits which a signal that the end of travel has been reached and the stage is then translated a short distance 282 in the X direction and a short distance 284 in the Y direction to define the first tile 288 in terms of a reference point 290 at its upper left hand corner. Since the size of the macro image tile 288 is known, the next macro image tile 292 may be placed contiguous with it by moving the stage appropriately and by measuring the location of the stage from the stage in counters without the necessity of performing any image manipulation. The image tiles 288 and 292 may be abutted without any substantial overlap or they may be overlapped slightly, such as a one pixel with overlap, which is negligible insofar as blurring of any adjacent edges of abutted image tiles i.e. a visually seamless, composite, macro image. The upper left hand corner 300 of the tile 292 defines the rest of the micro image tile 292 and other tiles can be so defined. Micro image tiles can likewise be defined so that they are contiguous but not substantially overlapping, as would interfere with the composite visually seamless, reconstructed image. This avoids the problems encountered with having to perform extended computations on digital images in a frame storer or multiple frame storage in order to match or bring the images into contiguity without blurriness at the edges of contiguous image tiles. It may be appreciated as shown in FIG. 2 that the low power image 24 has a plurality of micro images defined therein which are tiled and which are shown in higher magnification as individual tiles 312, 314, 316 and the like in FIG. 2. In addition, the region 310 when magnified as shown in the window 26 may exceed the bounds of the window and thus the window may include scroll bars or other means for allowing the image 310 which is larger than the window 26 to be examined from within the window 26.

Figure 11A:
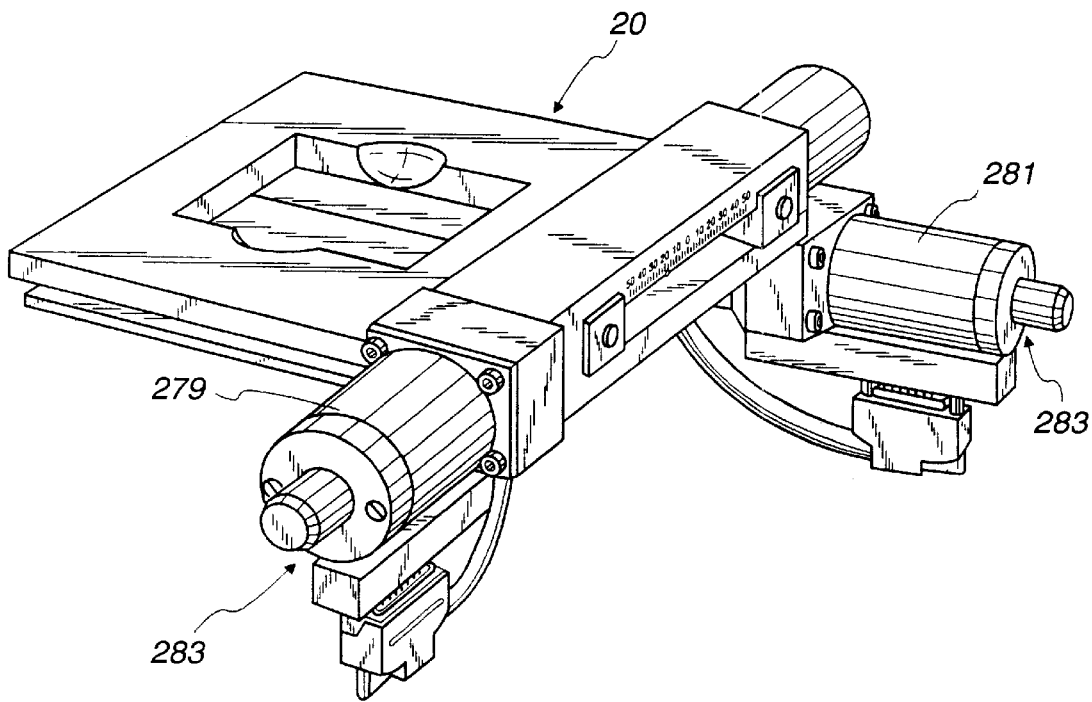
FIG. 11A is a perspective view of the microscope stage and stepper motors and encoders providing a closed loop drive for the motors.
Figure 12:
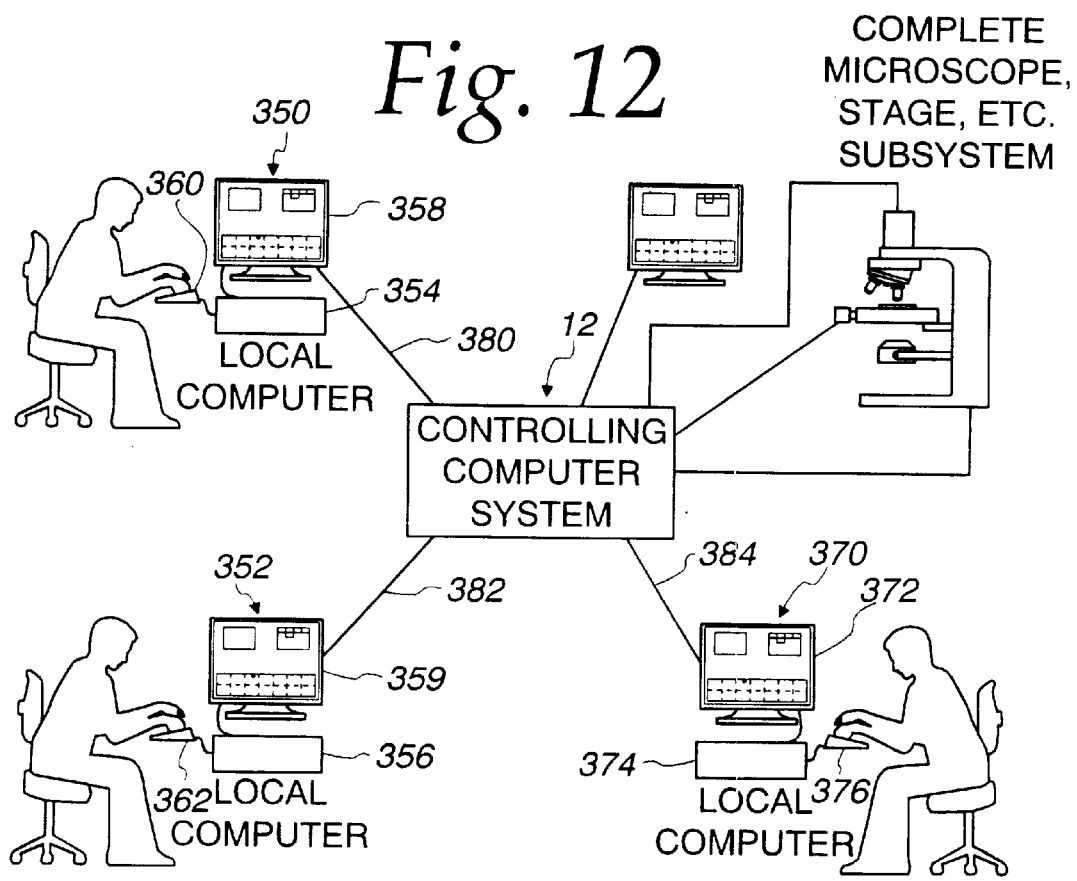
FIG. 12 is a block diagram of a networked system allowing multiple workstations to obtain access to diagnostic image information and to manipulate such information locally at such workstation.
Figure 12A:
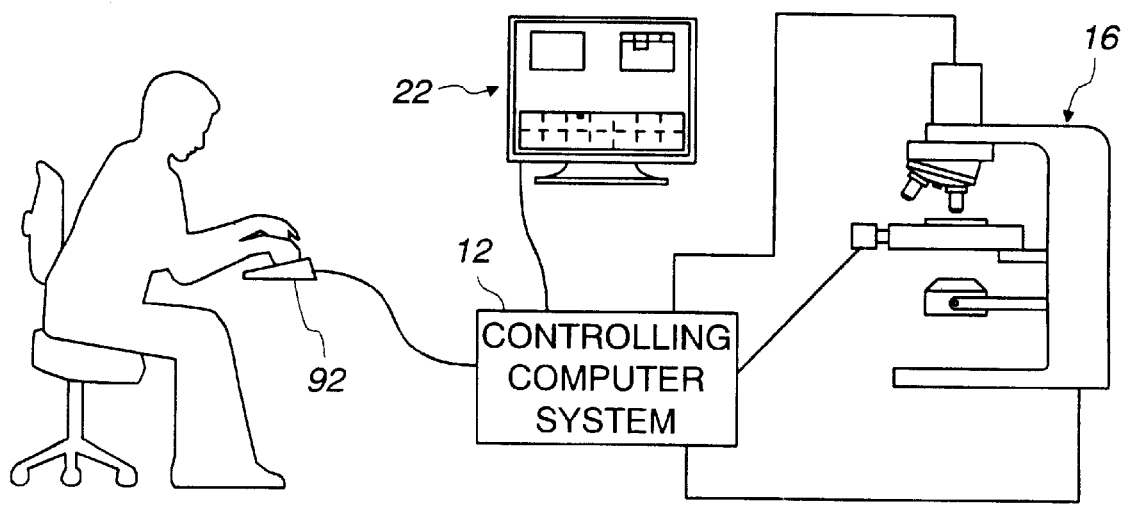
FIG. 12A is a view of the system described in connection with FIG. 5.

The stag 200 is best seen in FIG. 11A and includes the X and Y stepper motors 279 and 281 with their respective encoders, which provide a closed loop system to give the 0.1 micron accuracy versus the usual 5 or 6 micron accuracy of most microscope stages without a closed loops system. Thus, the X, Y stage has a higher positional, spatial resolution at 0.1 micron than the spatial pixel resolution of the CCD camera operating at the magnifications described herein. This closed loop system and this very high accuracy allow the abutting of the tile images for both high magnification and low magnification images without the substantial overlap and the time-consuming and expensive software currently used to eliminate the overlap and blurriness at the overlapping edges of adjacent image tiles. With the precisely positioned stage and by using the tiling system described in connection with FIG. 11, where the slide is precisely positioned relative to a center point CP for the slide, and the known position of point 278 is always taken from the same point, the tiles may be positioned precisely in a horizontal row and precisely in vertical rows to reconstruct the macro image and the micro image. This reconstruction is done without the use, as in the prior art, of extensive software manipulation to eliminate overlapping image tiles, horizontally or vertically or the haphazard orientation of image tiles.

Furthermore, as shown in FIG. 3, the low power window 24, high power window 26 and control window 28 can be used in conjunction with reporting of quantitative analysis data, histograms, etc. for the specimen being viewed; and such analysis information may be provided as a visual output in a window 320. Each of the various regions 30 that a pathologist may follow in marking various features in the low power window 24 and the high power window 26 may be reflected in both windows in order that an audit trail is provided for the system.

The present invention also includes the facility for allowing remote diagnostics to occur by being able to couple the system either over a network communication facility to an intranet, for instance via the network interface, or via a modem or other suitable connection, to an internet so that once the image has been scanned and stored in memory on hard disks or other storage, remote users may be able to access the low magnification image as well as the high magnification image and move around within both images to make determinations as to the histological characteristics of the samples via Z scores.

An additional feature of the system includes a plurality of networked workstations coupled to a first computer console 12 having a display screen 22 connected to the microscope 14. Satellite work stations 350 and 352 are substantially identical to the work station 12 including respective computers 354 and 356 coupled to displays 358 and 360. The devices can be manipulated through input devices 360 and 362 which may include a keyboard, mouse and the like. Also a third device can be connected including a work station 370, having a display 372, a computer 374 and an input device 376. Each of the devices is connected over respective network lines 380, 382, 384 to the computer 12 which transmission may be via Ethernet or the like. Each of the different operators at the physically separate viewing stations can locate regions from the view of entire tissue cross sections via a macro view and label the regions for subsequent scanning and/or quantitative analysis. A single operator at the instrument station 12 can locate regions to view the entire tissue cross section. Those regions can be labeled for subsequent scanning and/or quantitative analysis with subsequent review and physically remote viewing stations, for instance, in an operating room or in individual pathologists' signout areas in order to review analysis results while still maintaining and reviewing the entire macro view of the tissue and/or the individual stored images from which the quantitative results were obtained. The viewing stations 350, 352 and 370 can comprise desk top computers, laptops, etc. There is no need for a microscope at the network stations 350, 352 and 370.

In a still further alternative embodiment, remote workstations 400, 402, 404, 406 and 408 may be connected through a server 410 which may be supplied via a packet switched network. The server 410 and may be a hypertext transport protocol based server of the type used for the World Wide Web or may be a telnet type server as used previously in internet remote operation applications. The server 410 communicates via a communications channel 414 with a local computer 416 having a display 418 associated therewith, the local computer 416 being connected to the microscope 420. Each of the remote work stations 400, 402, 404, 406 and 408 may perform the same operations as the stations 350, 352 and 370 although they do it from nearby buildings or even from around the world, thus providing additional flexibility for others to make use of the specimen obtained and being viewed under the microscope 420. In addition, stored images may be disseminated through the server 410 to the remote servers 400 through 408 for further analysis and review.

Figure 14:
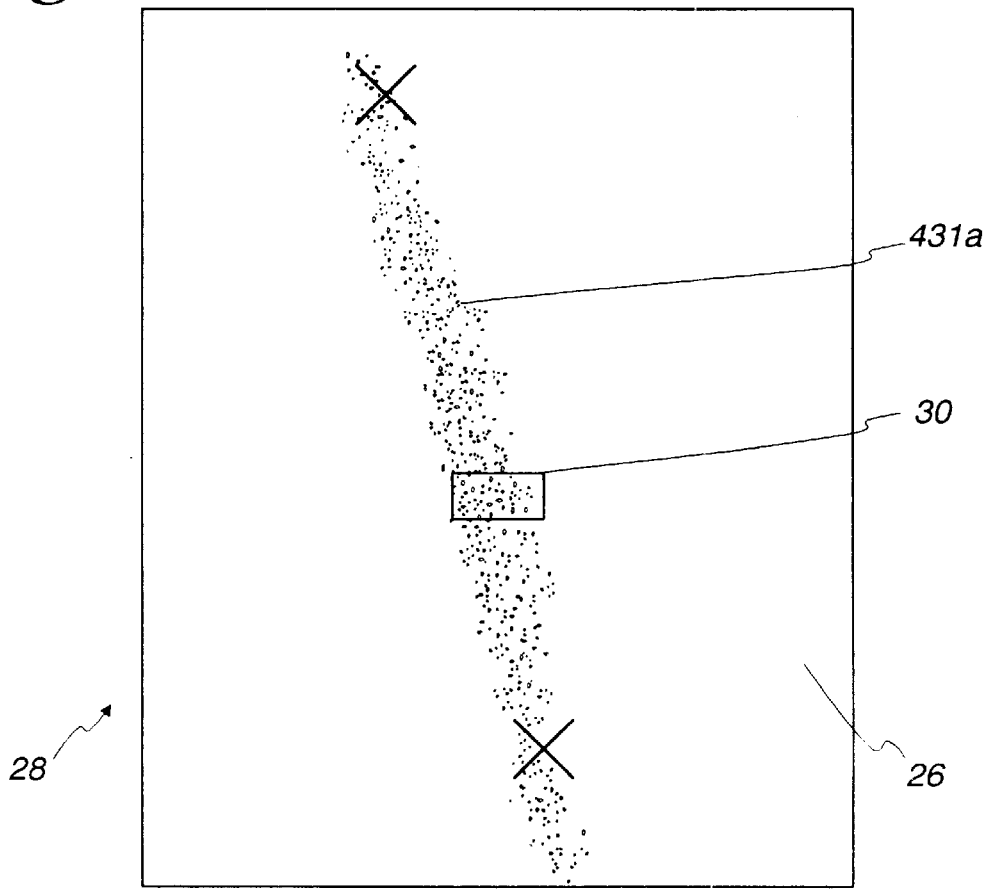
FIG. 14 is a view of a low magnification, reconstructed image from a basal layer of rat esophagus.
Figure 14A:
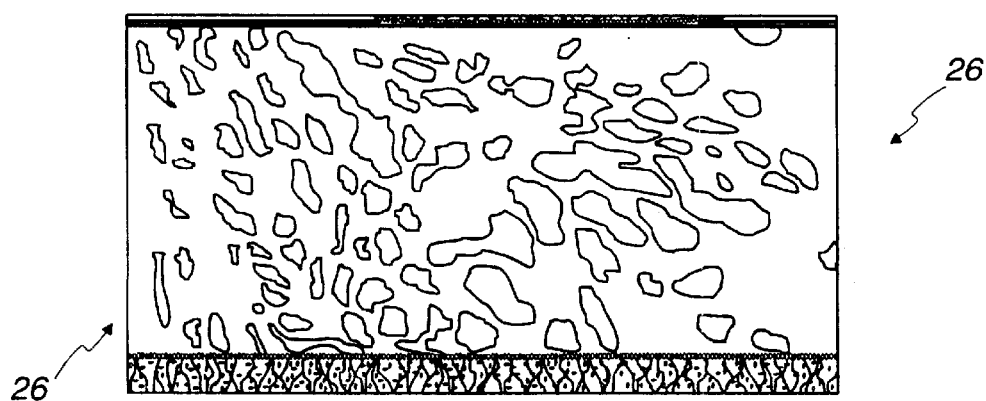
FIG. 14A is a view of a high magnification, reconstructed image from a selected point of interest from FIG. 14.
Figure 15A:
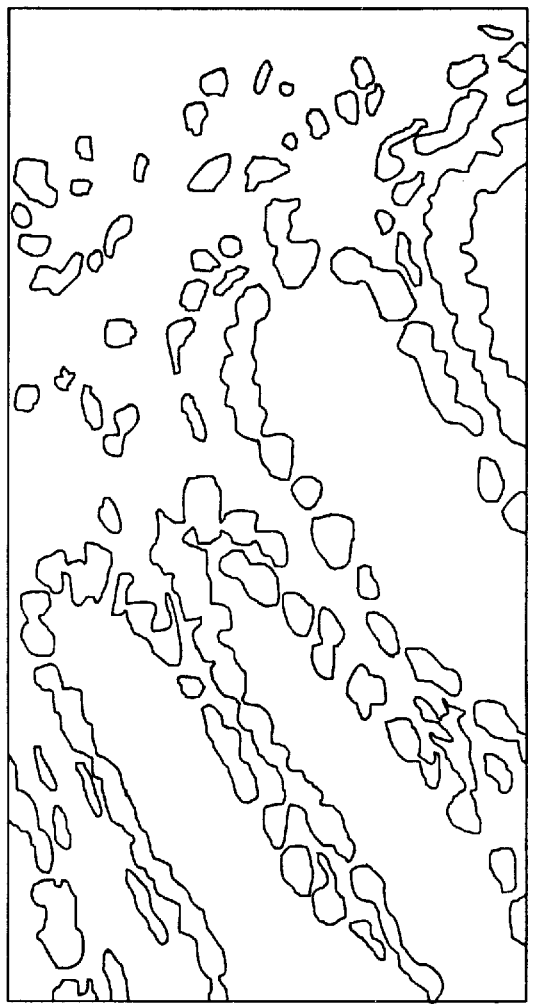
FIG. 15A is a view of a reconstructed macro image of a mouse colon.
Figure 15:
FIG. 15 is a view of a low magnification image of a mouse colon having a basal layer.

In FIG. 14, there is illustrated on screen 28 a basal layer 431a of a cut cross-section of a rat esophagus. The basal layer is elongated and linear in a downward direction, and the selected point of interest is shown as a box 30 on the basal layer on the composite, low magnification image. The high magnification image 26 of this selected point of interest is shown on screen 26 in FIG. 14A. In FIG. 15 is shown a mouse colon as a reconstructed, low magnification macro image 28 which has been reduced 1/16th in size. The micro image 26 is shown in FIG. 15A, and the marking therefore is shown in FIG. 15.

Figure 16:
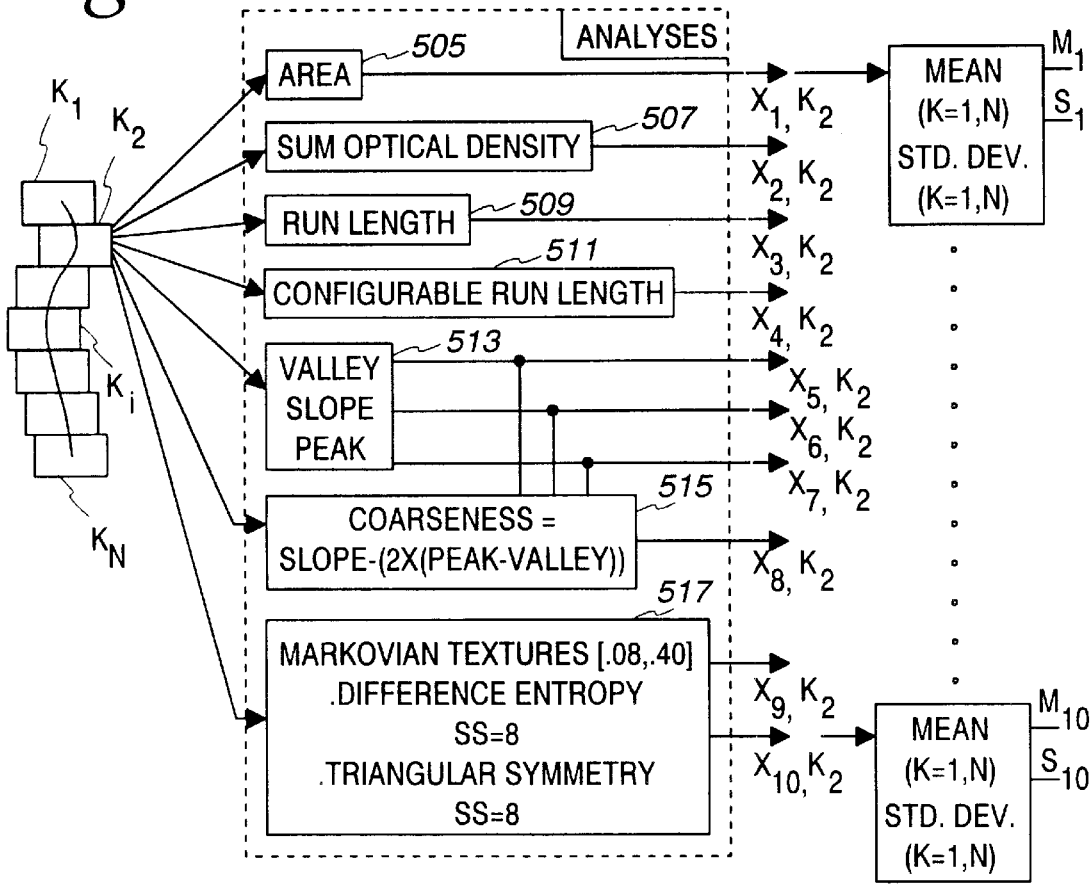
FIG. 16 is a schematic view of an analysis from regions of a basal layer.
Figure 16A:
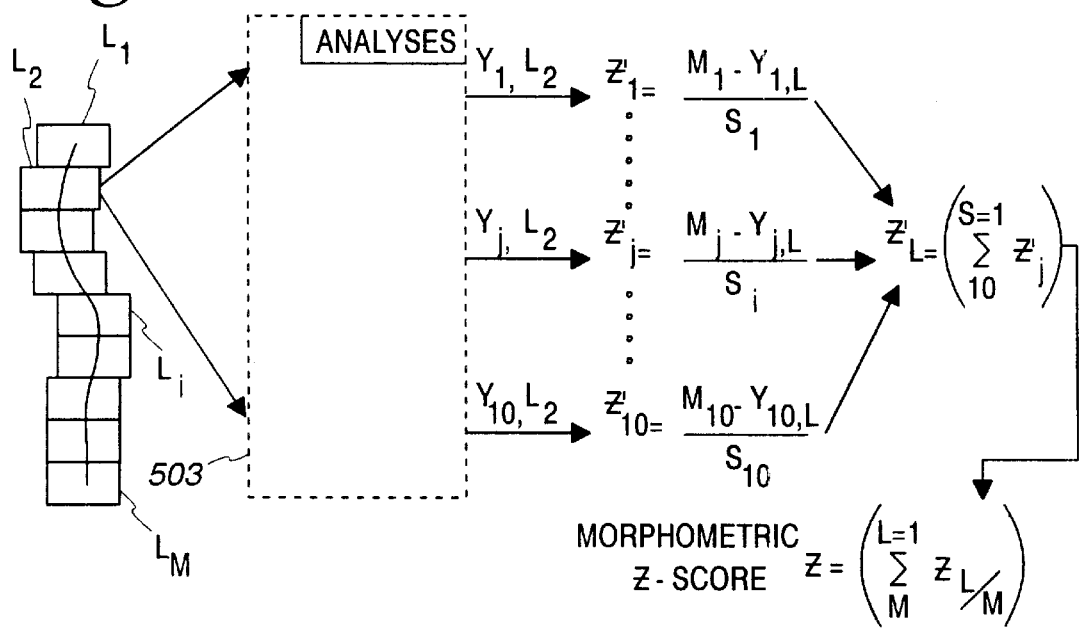
FIG. 16A is a schematic view of an analysis to provide to a Z score.
Figure 17:
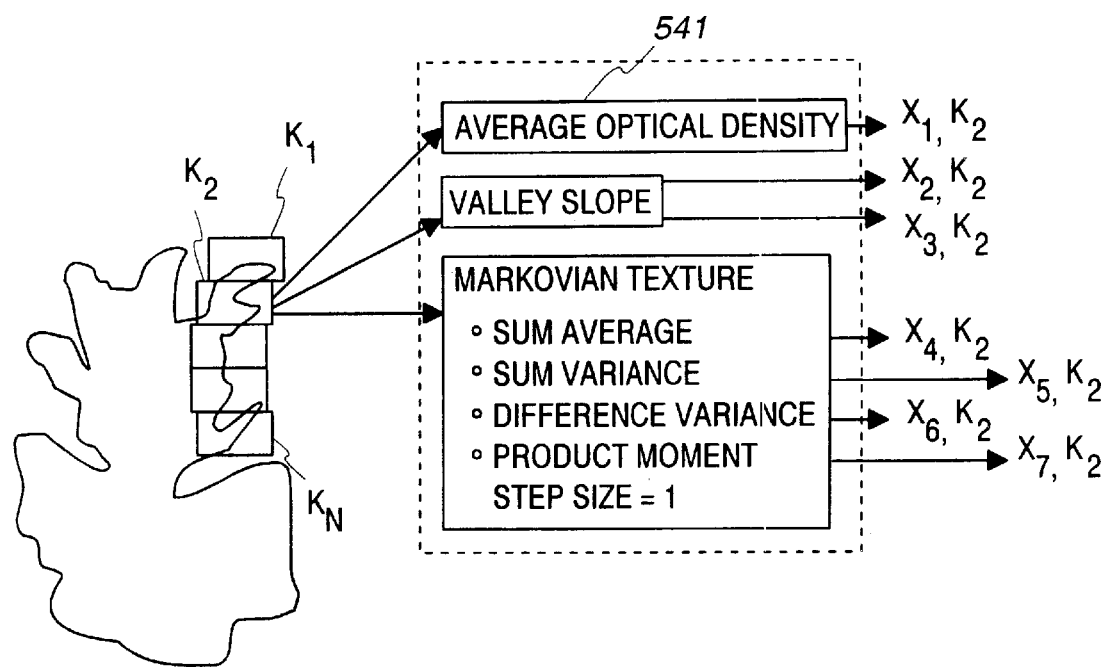
FIG. 17 is a schematic view showing texture analysis tests for regions.

The analysis for texture and for morphological features used to analyze a series of regions 30 on the elongated basal layer that were analyzed at high magnification are shown in FIGS. 16, 16A and 17. The manner of doing these tests and of obtaining a Z score or grade is disclosed in the aforesaid patent application.

While there has been illustrated and described a particular embodiment of the present invention, it will be appreciated that numerous changes and modifications will occur to those skilled in the art, and it is intended in the appended claims to cover all those changes and modifications which followed in the true spirit and scope of the present invention.

What is claimed is:

1. A method of using a computer controlled microscope imaging system to provide a reconstructed seamless image reconstructed from several contiguous fields of view showing the architecture and spatial relationship of biological material in a biological specimen, the method comprising:

scanning the specimen with a microscope at a predetermined magnification, optical resolution and pixel resolution and acquiring digitized image tiles of contiguous fields of view;

acquiring image registration information for the image tiles using microscope stage coordinates;

assembling and coordinating the digitized image tiles using a acquired image registration information to align respective edges of the contiguous image tiles to form a reconstructed seamless composite image formed of a plurality of digitized, contiguous image tiles;

displaying the reconstructed, seamless, composite image showing the architecture and the spatial relationship of the biological material in contiguous image tiles at an optical resolution for viewing and diagnostic analysis without the aid of a microscope;

scanning the specimen at a first prior time at a lower magnification and optical resolution and acquiring contiguous image tiles and acquiring image registration information for each of these lower magnification, image tiles to align the respective edges thereof;

assembling and coordinating the digitized, lower magnification, image tiles using the acquired image registration information to align respective edges of the contiguous image tiles to form a reconstructed, seamless, composite, lower magnification image formed of a plurality of digitized, contiguous, image tiles; and navigating within the specimen's composite, lower magnification and optical resolution image and selecting adjacent segments of the navigated area on the composite, overall specimen image for the tile image acquisition at a predetermined, higher predetermined magnification and optical resolution.

2. A method of using a computer controlled microscope imaging system to provide a reconstructed seamless image reconstructed from several contiguous fields of view showing the architecture and spatial relationship of biological material in a biological specimen, the method comprising:

scanning the specimen with a microscope at a predetermined magnification, optical resolution and pixel resolution and acquiring digitized image tiles of contiguous fields of view;

acquiring image registration information for the image tiles using microscope stage coordinates;

assembling and coordinating the digitized image tiles using the acquired image registration information to align respective edges of the contiguous image tiles to form a reconstructed seamless composite image formed of a plurality of digitized, contiguous image tiles;

displaying the reconstructed, seamless, composite image showing the architecture and the spatial relationship of the biological material in contiguous image tiles at an optical resolution for viewing and diagnostic analysis without the aid of a microscope; and scrolling by the user and displaying additional adjacent image tiles to the previously displayed fields of view to create a new composite image and to bring into view a further architecture and spatial relationship including the biological material displayed before and after scrolling the optical resolution for diagnostic analysis.

3. A method of using a computer controlled microscope imaging system to provide a reconstructed seamless image reconstructed from several contiguous fields of view showing the architecture and spatial relationship of biological material in a biological specimen, the method comprising:

scanning the specimen with a microscope at a predetermined magnification, optical resolution and pixel resolution and acquiring digitized image tiles of contiguous fields of view;

acquiring image registration information for the image tiles using microscope stage coordinates;

assembling and coordinating the digitized image tiles using the acquired image registration information to align respective edges of the contiguous image tiles to form a reconstructed seamless composite image formed of a plurality of digitized, contiguous image tiles;

scanning the specimen at a first prior time at a lower magnification and optical resolution and acquiring contiguous image tiles and acquiring image registration information for each of these lower magnification, image tiles to align the respective edges thereof;

assembling and coordinating the digitized, lower magnification, image tiles using the acquired image registration information to align respective edges of the contiguous image tiles to form a reconstructed, seamless, composite, lower magnification image formed of a plurality of digitized, contiguous, image tiles; and displaying the reconstructed, seamless, composite image showing the architecture and the spatial relationship of the biological material in contiguous image tiles at an optical resolution for viewing and diagnostic analysis without the aid of a microscope;

the scanning of the specimen at the predetermined magnification and optical resolution being done subsequent to the scanning of the specimen with a microscope at a lower magnification and optical resolution; and displaying each of the seamless, composite images at different magnifications and optical resolutions simultaneously to the viewer.

4. A method in accordance with claim 3 wherein:

the scanning of the specimen with a microscope at first and second magnifications and optical resolutions is done at a first location;

transmitting the digitized and stored contiguous fields of view and edge registering information to a remote location;

displaying each of the reconstructed, seamless, composite images simultaneously to the user; and interaction by the user with the composite, lower magnification seamless image at the remote location to provide new displays of seamless, reconstructed, composite images at the higher resolution to the remote viewer of adjacent segments of specimen.

5. A method of using a computer controlled microscope imaging system to provide a reconstructed seamless image reconstructed from several contiguous fields of view showing the architecture and spatial relationship of biological material in a biological specimen, the method comprising:

scanning the specimen with a microscope at a predetermined magnification, optical resolution and pixel resolution and acquiring digitized image tiles of contiguous fields of view;

acquiring image registration information for the image tiles using microscope stage coordinates;

assembling and coordinating the digitized image tiles using the acquired image registration information to align respective edges of the contiguous image tiles to form a reconstructed seamless composite image formed of a plurality of digitized, contiguous image tiles;

scanning the specimen at a first prior time at a lower magnification and optical resolution and acquiring contiguous image tiles and acquiring image registration information for each of these lower magnification, image tiles to align the respective edges thereof;

assembling and coordinating the digitized, lower magnification, image tiles using the acquired image registration information to align respective edges of the contiguous image tiles to form a reconstructed, seamless, composite, lower magnification image formed of a plurality of digitized, contiguous, image tiles;

displaying the reconstructed, seamless, composite image showing the architecture and the spatial relationship of the biological material in contiguous image tiles at an optical resolution for viewing and diagnostic analysis without the aid of a microscope; and forming a composite, magnified and reconstructed image at the lower magnification and lower resolution for displaying substantially the entire specimen to the observer.

6. A method of using a computer controlled microscope imaging system to provide a reconstructed seamless image reconstructed from several contiguous fields of view showing the architecture and spatial relationship of biological material in a biological specimen, the method comprising:

scanning the specimen with a microscope at a predetermined magnification, optical resolution and pixel resolution and acquiring digitized image tiles of contiguous fields of view;

acquiring image registration information for the image tiles using microscope stage coordinates;

assembling and coordinating the digitized image tiles using the acquired image registration information to align respective edges of the contiguous image tiles to form a reconstructed seamless composite image formed of a plurality of digitized, contiguous image tiles;

displaying the reconstructed, seamless, composite image showing the architecture and the spatial relationship of the biological material in contiguous image tiles at an optical resolution for viewing and diagnostic analysis without the aid of a microscope;

using an automated X, Y stage with higher positional spatial resolution than the spatial pixel resolution of a digital image scanner used to acquire the contiguous fields of view; and using the higher spatial resolution X, Y stage coordinates associated with each image tile as the registration information to reconstruct and display on a display monitor a visually seamless, reconstructed image formed of the contiguous, multiple fields of view.

7. The method of claim 6 including using stage-positional, spatial resolution of at least about 0.1 micron or less when acquiring image registration information to align respective edges of contiguous image tiles.

8. The method of claim 7 comprising using a closed loop stage drive system to provide the at least about 0.1 micron stage-positional, spatial resolution.

9. A computer controlled microscope imaging system to provide a reconstructed seamless image reconstructed from several contiguous fields of view showing the architecture and spatial relationship of biological material in a biological specimen, the system comprising:

a microscope for scanning the specimen at a predetermined magnification, optical resolution and pixel resolution for acquiring contiguous fields of view of the specimen;

an imaging subsystem including a digital image scanner connected to the microscope for acquiring digitized image tiles of contiguous fields of view, and for acquiring image registration information for the image tiles using microscope stage coordinates, and for assembling and coordinating the digitized image tiles using the acquired image registration information to align respective edges of the contiguous image tiles to form a reconstructed seamless composite image formed of a plurality of digitized, contiguous image tiles; and a display screen device for displaying the reconstructed, seamless, composite image showing the architecture and the spatial relationship of the biological material in contiguous image tiles at an optical resolution for viewing and diagnostic analysis without the aid of a microscope;

an automated X, Y stage with higher positional, spatial resolution than the spatial pixel resolution of the digital image scanner used to acquire the contiguous fields of view; and the display screen device using the higher spatial resolution X, Y stage coordinates associated with each image tile as the registration information to reconstruct and to display a visually seamless, reconstructed image formed of the contiguous, multiple filed of views.

10. The system of claim 9 wherein the automated X, Y stage has a positional, spatial resolution of at least about 0.1 micron or less when acquiring image registration information to align respective edges of contiguous image tiles.

11. The system of claim 10 wherein the X, Y stage comprises a closed loop stage drive system to provide the at least about 0.1 micron stage-positional, spatial resolution.

* * * * *